US 7,968,330 B2

(12) United States Patent
Nakamura et al.

(10) Patent No.: US 7,968,330 B2
(45) Date of Patent: Jun. 28, 2011

(54) CULTURE OBSERVATION EQUIPMENT

(75) Inventors: Kyoji Nakamura, Koza-gun (JP); Takayuki Uozumi, Machida (JP)

(73) Assignee: Nikon Corporation, Tokyo (JP)

( * ) Notice: Subject to any disclaimer, the term of this patent is extended or adjusted under 35 U.S.C. 154(b) by 234 days.

(21) Appl. No.: 12/216,885

(22) Filed: Jul. 11, 2008

(65) Prior Publication Data

US 2008/0293131 A1    Nov. 27, 2008

Related U.S. Application Data

(63) Continuation of application No. PCT/JP2007/000171, filed on Mar. 6, 2007.

(30) Foreign Application Priority Data

Mar. 14, 2006   (JP) ................... 2006-069030

(51) Int. Cl.
*C12M 1/34* (2006.01)
*C12M 3/00* (2006.01)
*G02B 21/00* (2006.01)
(52) U.S. Cl. .................... 435/288.7; 359/368
(58) Field of Classification Search ............... 435/288.7; 359/368
See application file for complete search history.

(56) References Cited

U.S. PATENT DOCUMENTS

| 4,090,921 | A  | * | 5/1978  | Sawamura et al. | ........ 435/286.2 |
| 7,141,413 | B2 |   | 11/2006 | Yamamoto et al. |                    |
| 2004/0152188 | A1 | * | 8/2004  | Yamamoto et al. | ........ 435/287.3 |
| 2005/0105172 | A1 | * | 5/2005  | Hasegawa et al. | ............ 359/368 |
| 2006/0128005 | A1 | * | 6/2006  | Hasegawa et al. | ........ 435/286.2 |

FOREIGN PATENT DOCUMENTS

| JP | A-58-155087 | 9/1983 |
| JP | A-58-159513 | 9/1983 |
| JP | A-2004-180675 | 7/2004 |
| JP | A-2005-326495 | 11/2005 |

* cited by examiner

*Primary Examiner* — Walter D Griffin
*Assistant Examiner* — Lydia Edwards
(74) *Attorney, Agent, or Firm* — Oliff & Berridge, PLC

(57) ABSTRACT

The present application includes a culture chamber, an observation chamber having an optical system of observation to observe samples to be cultured in the culture chamber, and a movement stage provided at a boundary which separates the culture chamber and the observation chamber, functioning as a wall to maintain an environment of both of the chambers, bearing the samples, and moving the samples on a light axis of observation of the optical system of observation. Due to such an arrangement, a culture observation equipment which has good response and excellent environmental resistance can be achieved, preventing problems such as the overall size of the device became large, maintenance work was difficult, and device cost became expensive.

9 Claims, 8 Drawing Sheets

(a)

(b)

(a)

(b)

CULTURE OBSERVATION EQUIPMENT

CROSS-REFERENCE TO RELATED APPLICATION

This application is a Continuation Application of International Application No. PCT/JP2007/000171, filed Mar. 6, 2007, designating the U.S., in which the International Application claims a priority date of Mar. 14, 2006, based on prior filed Japanese Patent Application No. 2006-069030, the entire contents of which are incorporated herein by reference.

BACKGROUND

1. Field

The present application relates to a culture observation equipment which has an optical device such as a microscope.

2. Description of the Related Art

In recent years, research and development of cell culture has been spread widely in the field of regenerative medicine and drug development, where culture devices (incubators) which culture cells and observation equipments such as a microscope to observe cell situation are used. Conventionally, when samples during culture in an incubator are observed, a holder containing samples is taken out from a culture chamber temporarily to be placed on an observation stage for observation, and thereafter the holder is returned to the culture chamber again.

Further, in Patent Document 1 (Japanese Unexamined Patent Application Publication No. 2004-180675), a microscope is placed in a shield case separating the microscope from the culture chamber so that the environment in the culture chamber is not fluctuated, hence optical devices are not damaged.

In Patent Document 1, a microscope unit can be moved in the three dimensional direction, X, Y and Z, so as to advance towards the observation part, accordingly, working distance can be shortened. However, such a stage mechanism is required that has a large driving power to drive the whole microscope unit in the three dimensional directions, X, Y and Z. Therefore, when moving among the observation points, there is a task to improve quick response.

In view of the above task, it is the proposition to provide a culture observation equipment with high response performance and excellent environmental resistance.

An culture chamber includes an culture chamber, an observation chamber having an optical system of observation to observe samples cultured in the culture chamber, and a movement stage provided at a boundary which separates the culture chamber and the observation chamber, functioning as a wall to maintain an environment of both chambers, bearing the samples, and moving the samples on a light axis of observation of the optical system of observation in an orthogonal direction thereto.

Particularly, the movement stage is arranged to be coupled to a connecting material which is elastic and forms a boundary between the culture chamber and the observation chamber.

Further, the connecting material is made up of an elastic material having elasticity.

Alternatively, the connecting material includes a plate material which supports the movement stage and shielding liquid which lies between the movement stage and the plate material.

Particularly, the elastic material is made up of rubber provided with flexure being elastic in all circumferential directions.

Further, a section of the elastic material in a direction of expanding and shrinking is formed to have a rectangular shape.

In addition, the culture observation equipment includes driving units to drive the movement stage in horizontal direction so as to move a target point of observation of the sample, and optical driving units to drive the optical system of observation in vertical direction so as to focus on the sample.

Particularly, the movement stage is made up of transparent material and a fixed partition around the movement stage is made up of light shielding material.

Further, the connecting material is made up of low reflection and light shielding material.

SUMMARY

A movement stage, on which samples are placed and which is coupled to the fixed partition with an elastic material, can be moved freely while the culture chamber and the observation chamber are separated, and therefore a culture observation equipment which has good response as well as excellent environmental resistance can be achieved.

DETAILED DESCRIPTION OF THE EMBODIMENTS

Hereinafter, detailed description of a culture observation equipment will be described with reference to attached drawings.

First Embodiment

Figure 1:
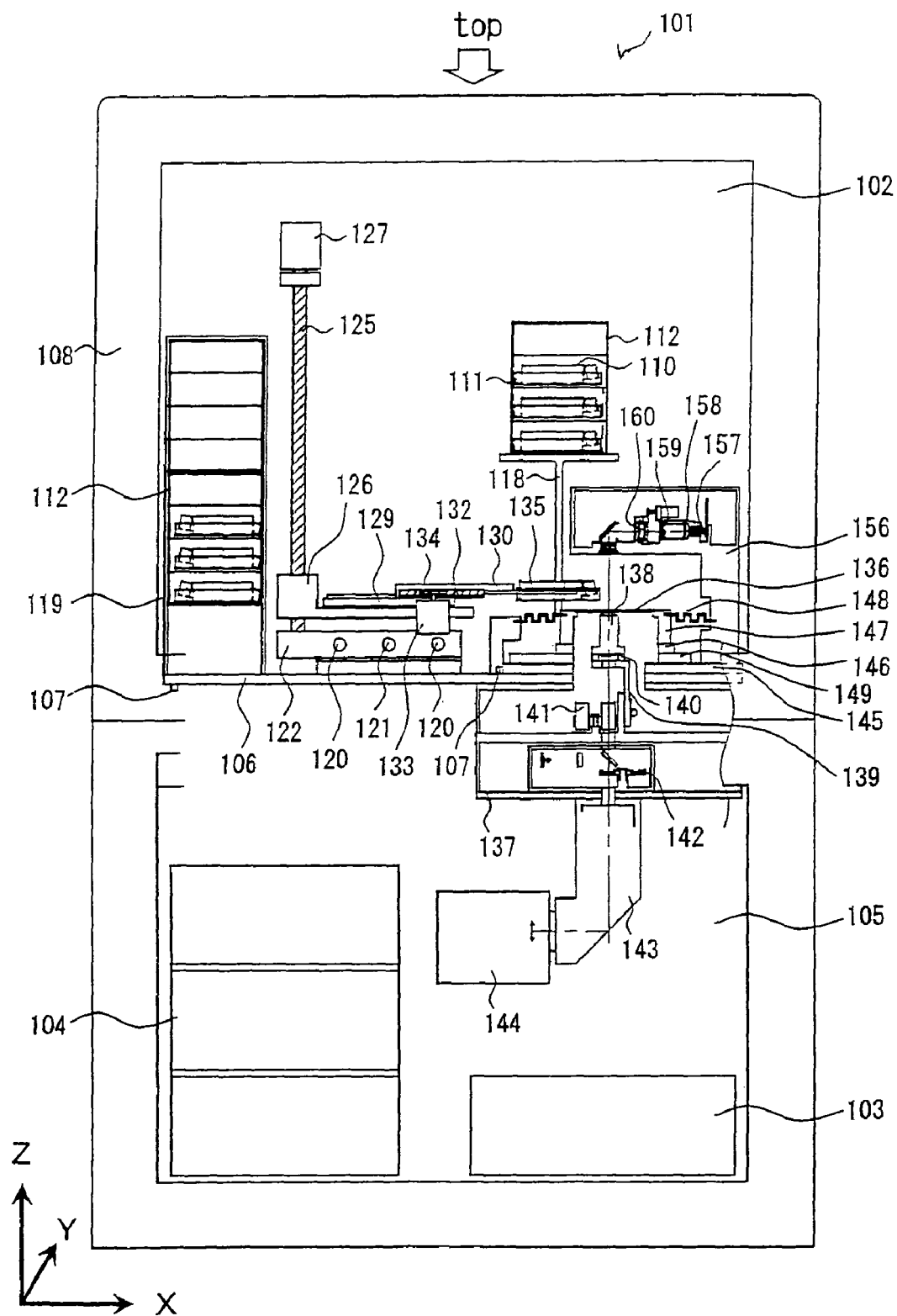
FIG. 1 is a front view of a culture observation equipment.
Figure 2:
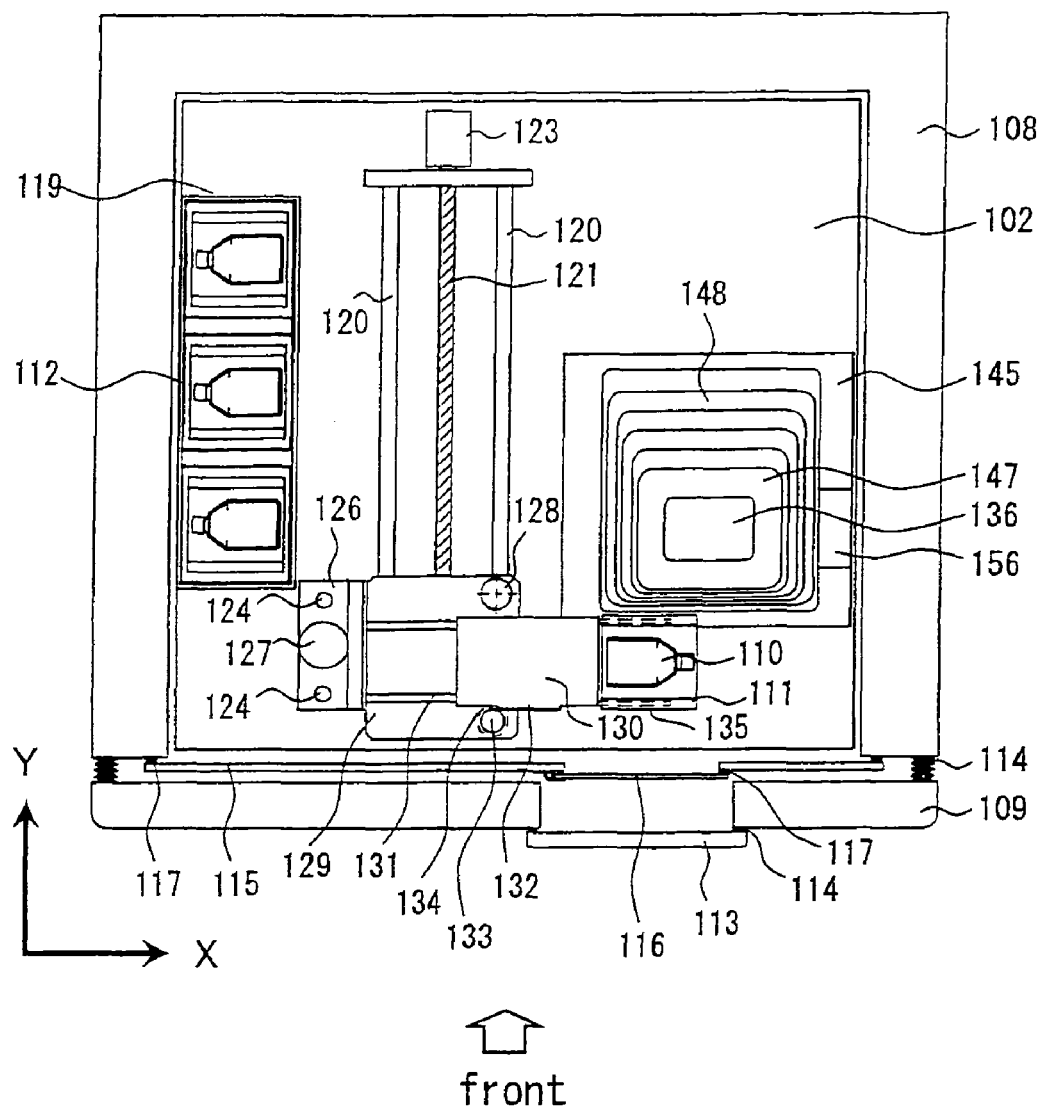
FIG. 2 is a top plan view of the culture observation equipment.

FIG. 1 is a front view of a culture observation device 101 according to the first embodiment, and FIG. 2 is a top view thereof. The culture observation device 101 according to the first embodiment is arranged to have an culture chamber 102 in the upper part thereof, and an observation chamber 105 that includes a personal computer 103, a controller 104 and the like in the lower part thereof. Between the culture chamber 102 and the observation chamber 105, a base plate 106 is fixed to a housing case 108 via a gasket 107, so that the humidity in the culture chamber 102 does not diffuse into the observation chamber 105.

In FIG. 2, an external door 109 of the culture chamber 102 is provided with an external small door 113 for carrying a carrier 112 shown in FIG. 1 into the culture chamber 102. In addition, heat-resistant gaskets 114 are provided respectively between the housing case 108 and the external door 109 as well as between the external door 109 and the external small door 113. Further a glass door 115 is provided inside of the external door 109, and in the glass door 115, at the corresponding position to the external small door 113, a small glass door 116 is attached. Gaskets 117 for seal-up are attached at the outer circumference of the glass door 115 and the glass small door 116.

As described above, complete seal-up of the culture chamber 102 achieves such a structure that the fluctuation of environment within the culture chamber 102 is suppressed as small as possible.

The environment in the culture chamber 102 is maintained at 37 degree C. in temperature, 90 percent in humidity, and ambient atmosphere of $CO_2$. Temperature management is carried out by temperature-controlled air flow within the housing case 108.

In FIG. 1, firstly holders 111, on which containers 110 having cells ready to start culture are placed, are put down on a carrier 112 as a batch of multiple holders and carried into a transferring rack 118, while the external small door 113 and the glass small door 116 of the culture chamber 102 are opened. Note that the carrier 112 has a role of a carrying case in carrying the holders 111.

Subsequently, the holder 111, on which the container 110 is placed, is taken out from the carrier 112 that was carried into the transferring rack 118 by an automatic transportation unit, and is stored in a holder storage cabinet 119 that is arranged at an internal side wall of the culture chamber 102. Here, the holder storage cabinet 119 includes the carriers 112 that can accommodate multiple holders 111, and samples such as cells are placed in the holder storage cabinet 119 to be cultured. Note that the holder 111 contains necessary culture fluid.

The automatic transportation unit includes driving parts for the triaxial direction of X axis direction, Y axis direction and Z axis direction, and a rotating direction. On the base plate 106, there is a driving part of Y axis direction, and Y axis moving stage 122 is attached to guide axis 120 and a driving shaft 121, the driving shaft 121 being rotated by a motor 123 to move the Y axis moving stage 122. As for Z axis direction, a Z axis moving stage 126 is attached to a guide axis 124 and a driving shaft 125 on the Y axis moving stage 122, and the Z axis moving stage 126 is moved by rotation of the driving shaft 125 with a motor 127.

A lower side of the X axis moving stage 129 is attached onto the Z axis moving stage 126 via a rotating shaft (not shown), and a rotating motor 128 can rotate the lower side of the X axis moving stage 129. In other words, the lower side of the X axis moving stage 129 can be turned toward the side of the transferring rack 118 or toward the side of the holder storage cabinet 119. An upper side of the X axis moving stage 130 placed on a guide rail 131 on the lower side of the X axis moving stage 129 can be moved in the direction of X axis through driving a rack 132 provided on a side of the upper side of the X axis moving stage 130 by a pinion 134 of a motor 133.

In addition, an arm 135 is attached on a top point of the X axis moving stage 130. The arm 135 enters under a rib portion of the holder 111 to support the holder 111 so as to transfer the holder 111 having the container 110 thereon.

Now, a series of carrying-in procedures of the container 110 that holds cells to be cultured into the culture chamber 102 will be described. An operator opens the external small door 113 and the glass small door 116, loads the container 110 placed on the holder 111 in the carrier 112, places the whole carrier 112 on the transferring rack 118 in the culture chamber 102, and closes the external small door 113 and the glass small door 116.

Subsequently, the automatic transportation unit is operated to move the Y axis moving stage 122 to meet a Y axis coordinate position of the holder 111 stacked in the carrier 112 on the transferring rack 118. Next, the Z axis moving stage 126 is moved in the direction of Z axis to the height of the holder 111 stacked in the carrier 112 on the transferring rack 118. The height thereof is equal to the height where the arm 135 at the upper side of the X axis moving stage 130 can be inserted under the rib of the holder 111 with a slight gap. In addition, the upper side of the X axis moving stage 130 has been already turned to the direction of the transferring rack 118.

In that state, the upper side of the X axis moving stage 130 is moved in the direction of X axis to insert the arm 135 under the rib of the holder 111 stacked in the carrier 112 on the transferring rack 118. In that situation, the Z axis moving stage 126 is raised a little so that the arm 135 can bring up the holder 111 slightly. When the arm 135 comes to support the holder 111, the upper side of the X axis moving stage 130 is drawn back from the transferring rack 118 to take out completely the holder 111 from the carrier 112 on the transferring rack 118.

After taking out the holder 111, the upper side of the X axis moving stage 130 is turned towards the holder storage cabinet 119. Following that, the Y axis moving stage 122 is moved to meet a position on the Y axis of a targeted carrier 112 in the holder storage cabinet 119. Then the Z axis moving stage 126 is moved in the direction of Z axis up to a height of the targeted carrier 112 in the holder storage cabinet 119. This height is such that the bottom of the holder 111 has a small gap above the shelf position of the targeted carrier 112. In this situation, the upper side of the X axis moving stage 130 is moved towards the side of the holder storage cabinet 119 in the X axis direction to bring in the holder 111 into the targeted carrier 112. After carrying the holder 111 into the targeted carrier 112, the Z axis moving stage 126 is lowered until the bottom of the holder 111 comes into contact with the shelf of the targeted carrier 112. When the arm 135 is detached from the rib of holder 111, the upper side of the X axis moving stage 130 is withdrawn from the holder storage cabinet 119 in a departing direction to complete a storage of the holder 111 to the carrier 112 in the holder storage cabinet 119.

Now, when the cells under culture in the holder storage cabinet 119 is to be observed, the holder 111 is taken out from the holder storage cabinet 119 and moved onto the transparent glass stage plate 136, which is an observation stage. Procedure of the automatic transportation unit in that event is identical with the procedure where the holder 111 is stored in the holder storage cabinet 119 from the transferring rack 118, accordingly the description thereof is omitted. Electric heat wires (heater) for condensation proof are stuck on the rear surface of the transparent glass stage plate 136, the wires being disposed in a toric form so as not to disturb effective luminous flux in a center of light axis for observation.

Next, an observation chamber 105 of the culture observation device 101 will be described. Referring to FIG. 1, in the observation chamber 105 as an optical system of observation, an observation support stand 137 is fixed to the base plate 106 and optical components are disposed on the observation support stand 137, and thus the microscope is formed. The objective lens 138 of the microscope can be exchanged with a guide rail 140 on an objective lens support stand 139, and the objective lens support stand 139 is provided with an upper and lower mechanism for focus adjustment. Further behind the objective lens 138, a plurality of middle variable lenses 141 are provided on an electrically driven turret, so that a lens can be exchanged by electrical arrangement. In addition, a fluorescent lighting unit 142 is attached under the electrically driven turret.

In addition, a CCD support stand 143, in which optical material such as lenses, reflectors are assembled, is attached to the observation support stand 137 located under the fluorescent lighting unit 142 so that imaging is performed in a CCD camera 144. In the lower part of the observation chamber 105, a personal computer 103 for processing the observation images shot by the CCD camera 144 and a controller 104 in which a device for maintaining the environment of the culture chamber 102, power supply and the like are stored, are provided.

Moreover, there is an opening for observation by the microscope in a part of the base plate 106 between the culture chamber 102 and the observation chamber 105, and around the opening, a stage support stand 145 integrated onto the base plate 106 via a gasket 107 is fixed.

In addition, on the stage support stand 145, a stage plate 149, an X stage 146 and a Y stage 147 are provided. Aluminum material is used for weight saving as structural material of each stage. Note that the stage support stand 145, the stage plate 149, X stage 146 and Y stage 147 have also openings for observation by the microscope, and to the opening portion of the upper-most Y stage 147, a transparent glass stage plate 136 is stuck, which is to be an observation stage, and thereby airtightness is conserved. By the way, the electric heat wires of the transparent glass stage plate 136 are for heating the observation stage not to cause dew condensation in the culture chamber 102, which is in high humidity. Further, an elastic material 148 is attached between the Y stage 147 and the stage support stand 145 as a connecting material to couple the both, thereby providing such an arrangement as to separate atmosphere completely between the culture chamber 102 and the observation chamber 105. Incidentally, a column 156 is integrated onto a part of the stage support stand 145 to attach a lighting part.

Figure 3:
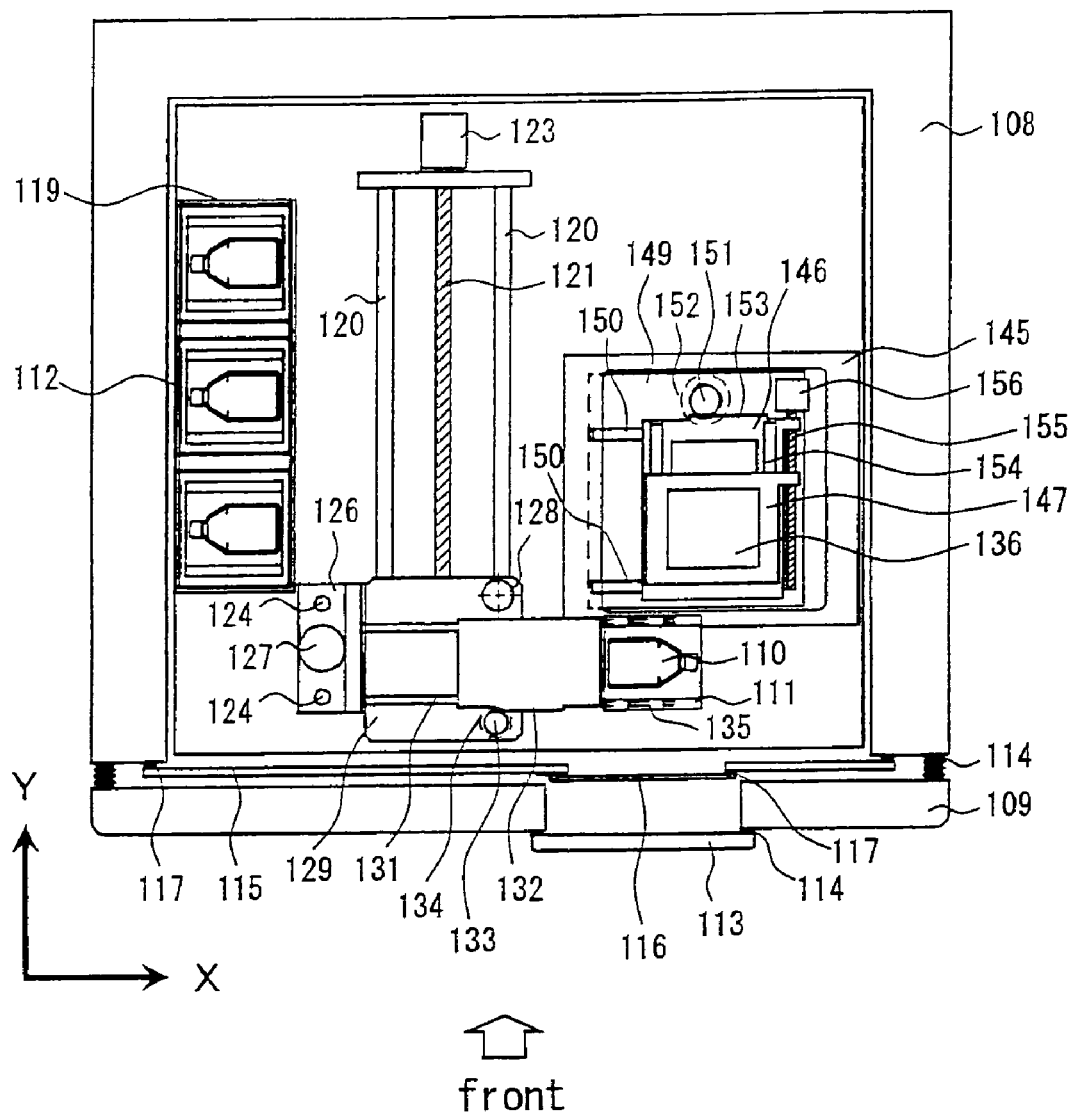
FIG. 3 is a top plan view of the culture observation equipment in a state where an elastic material is removed.

Next, structure of the X stage 146 and the Y stage 147 will be described. FIG. 3 is a top plan view when the elastic material 148 of FIG. 2 is removed. The stage plate 149 fixed on the stage support stand 145 lies in the very bottom and the X stage 146 is mounted on two guide rails 150 on the stage plate 149. As for the X stage 146, a motor 152, to which a pinion 151 on the stage plate 149 is attached, rotates to drive a rack 153 provided on a side of the X stage 146, and thus the X stage 146 is moved in the X axis direction. The Y stage 147 is mounted on two guide rails 154 and a driving shaft 155, and a motor 156 rotates the driving shaft 155 to move the Y stage 147 in the Y axis direction.

The holder 111, which has been transferred by the automatic transportation unit, is positioned on the transparent glass stage plate 136 and can be observed by the objective lens 138 of the microscope. As for lighting from the upper part in an occasion of observation, an LED 157 is mounted in a seal-up portion fixed to the base plate 106 via a pole 156. The light emitted from the LED 157 passes through a rectangular aperture 158, a phase ring 159 and a lighting objective lens 160 and lights cells in the container 110 on the holder 111.

Figure 4:
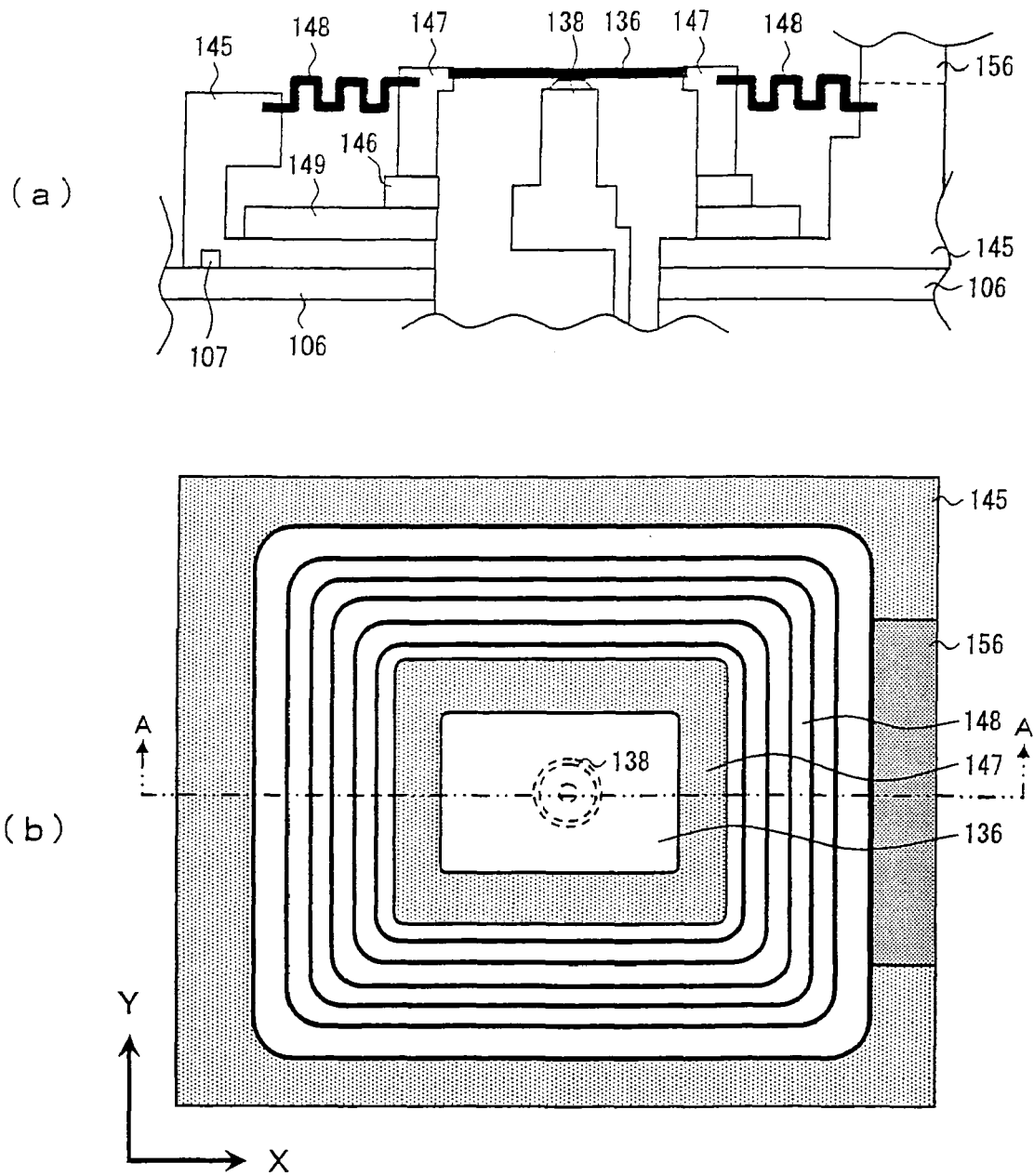
FIGS. 4(a) and 4(b) are diagrams for illustrating a shape of the elastic material.

Now, an elastic material 148, which is a structural element of the culture observation device 101, will be described in detail. FIGS. 4(a) and 4(b) are diagrams showing an enlarged circumference area of the elastic material 148 in FIG. 1. FIG. 4(a) is a cross section view in the X axis direction when the top view of FIG. 4(b) is cut along a cross section A. The elastic material 148 is provided between the Y stage 147 and the stage support stand 145 and is elastic in the direction of X axis, Y axis and in a diagonal direction. Note that the connecting position of the fixing side of the elastic material 148 is not always on the stage support stand 145 but any portion will do, which is fixed part to the housing case 108 and where seal-up can be executed. Similarly, the connecting position of the moving side is not always on the Y stage 147 but any portion will do, which is movable and where seal-up can be executed such as the transparent glass stage plate 136.

Figure 5:
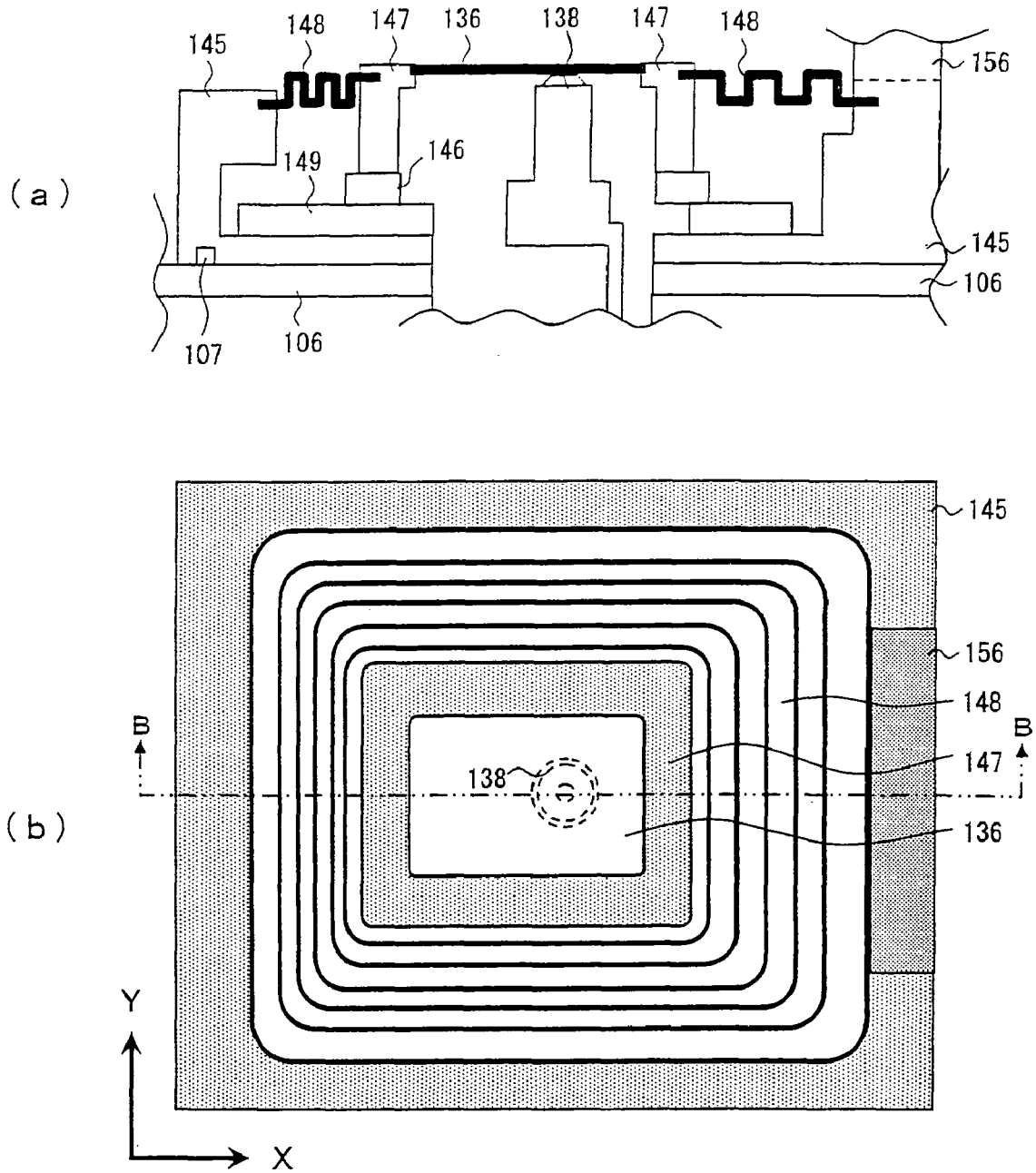
FIGS. 5(a) and 5(b) are diagrams for illustrating a state of the elastic material being elastic.

Next, a situation where the elastic material 148 is expanded will be described. FIGS. 5(a) and 5(b) show a situation when the Y stage 147 and the transparent glass stage plate 136 are moved to the left side in the X axis direction. FIG. 5(a) is a cross section view in the X axis direction when FIG. 5(b) is cut along a cross section B. The left side of the elastic material 148 is in a shrinkage situation where flexure is compressed, and conversely the right side of the elastic material 148 is in an extended situation where flexure is expanded. As described above, the transparent glass stage plate 136, which is integrated with the Y stage 147, can be moved towards the left side while keeping the culture chamber 102 and the observation chamber 105 completely separated from each other. As a result, the objective lens 138 comes to a situation of being moved towards right side relatively, allowing the objective lens 138 of the microscope to be aligned to the right side of the sample and thus observation can be performed.

FIGS. 6(a) and 6(b) show a situation where the Y stage 147 and the transparent glass stage plate 136 are moved to the right side in the X axis direction. FIG. 6(a) is a cross section view in the X axis direction when FIG. 6(b) is cut along a cross section C. Conversely to the situation of FIG. 5(a), the right side of the elastic material 148 is in a shrinkage situation where flexure is compressed, and conversely the left side of the elastic material 148 is in an extended situation where flexure is expanded. As described above, the transparent glass stage plate 136, which is integrated with the Y stage 147, can be moved towards the right side while keeping the culture chamber 102 and the observation chamber 105 completely separated from each other, and observation can be performed while the objective lens 138 of the microscope is aligned to the left side of the sample.

FIG. 7(a) shows a situation of the elastic material 148 where the Y stage 147 and the transparent glass stage plate 136 are moved toward the upper side in the Y axis direction. The upper side of the elastic material 148 is in a shrinkage situation where flexure is compressed, and conversely the lower side of the elastic material 148 is in an extended situation where flexure is expanded. Similarly to the previous case, the transparent glass stage plate 136, which is integrated with the Y stage 147, is moved toward the upper side while keeping the culture chamber 102 and the observation chamber 105 completely separated from each other, and observation can be performed while the objective lens 138 of the microscope is aligned to the lower side of the sample.

FIG. 7(b) shows a situation of the elastic material 148 where the Y stage 147 and the glass heater are moved towards right and lower side diagonally. The lower side, the right side, and the diagonally lower and the right side of the elastic material 148 are in a shrinkage situation where flexure is compressed, and conversely the upper side, the left side and the diagonally upper and the left side of the elastic material 148 is in an extended situation where flexure is expanded. Similarly to the other cases, the transparent glass stage plate 136, which is integrated with the Y stage 147, is moved towards the right and lower side diagonally while keeping the culture chamber 102 and the observation chamber 105 being completely separated from each other, and observation can be performed while the objective lens 138 of the microscope is aligned to the left and upper side of the sample.

Figure 6:
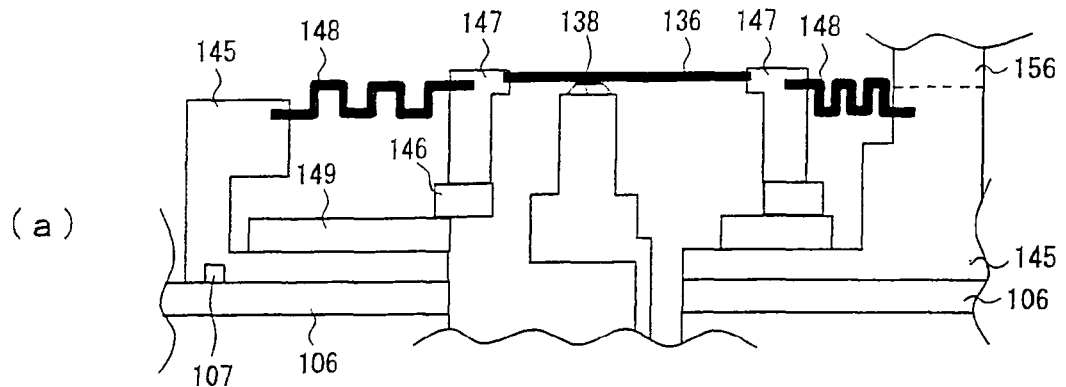
FIGS. 6(a) and 6(b) are diagrams for illustrating a state of the elastic material being elastic.
Figure 6:
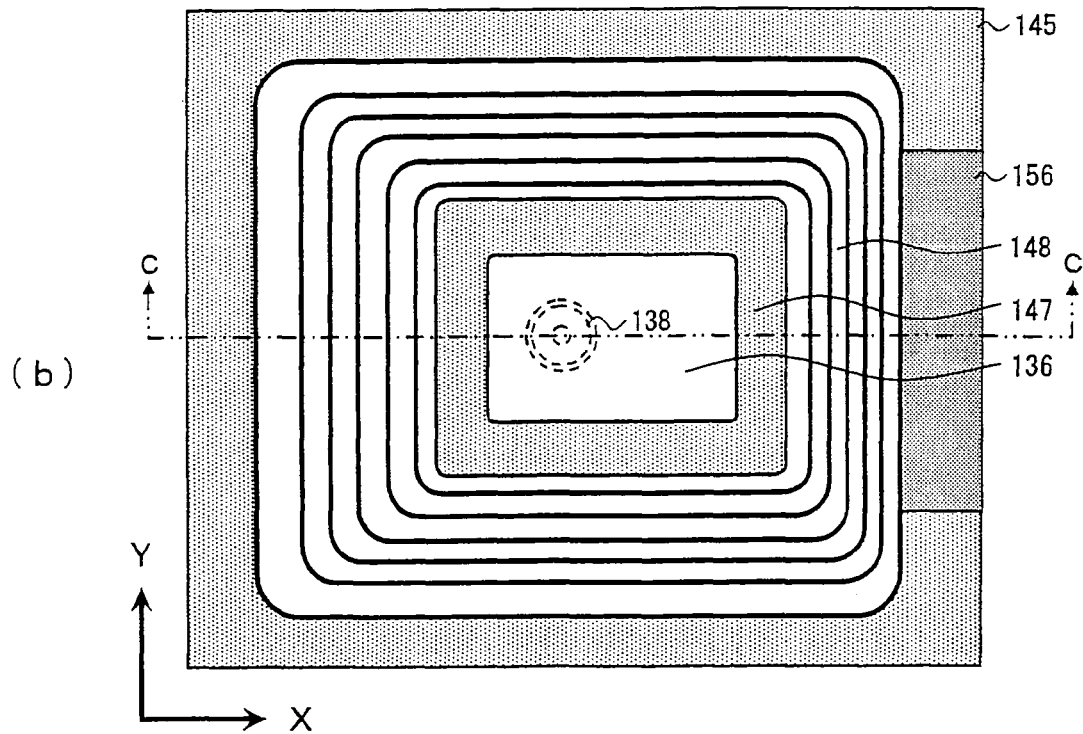
Figure 7:
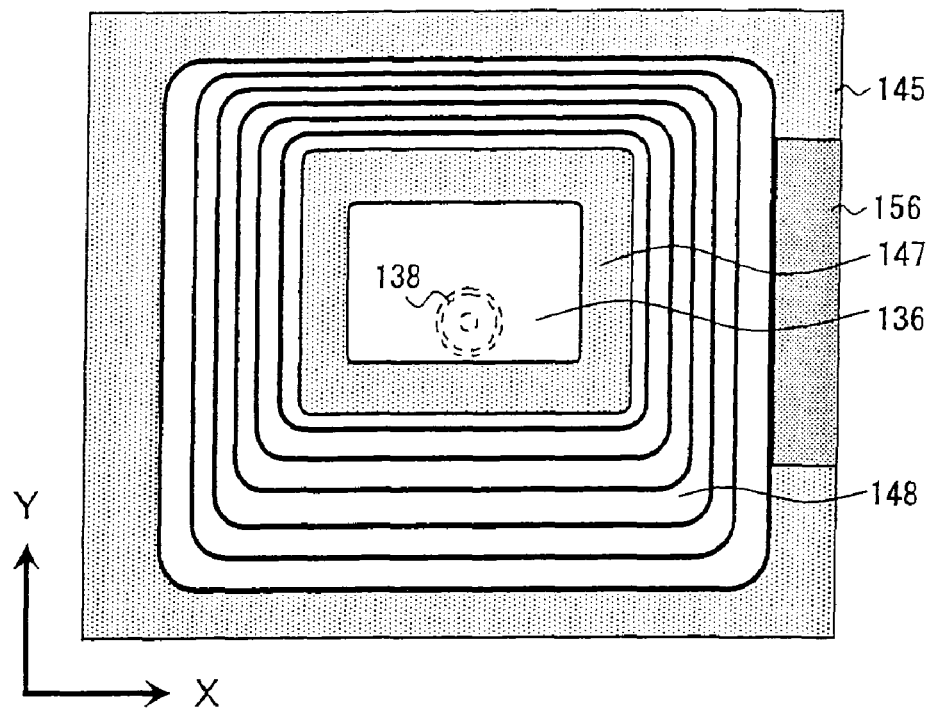
FIGS. 7(a) and 7(b) are diagrams for illustrating a state of the elastic material being elastic.
Figure 7:
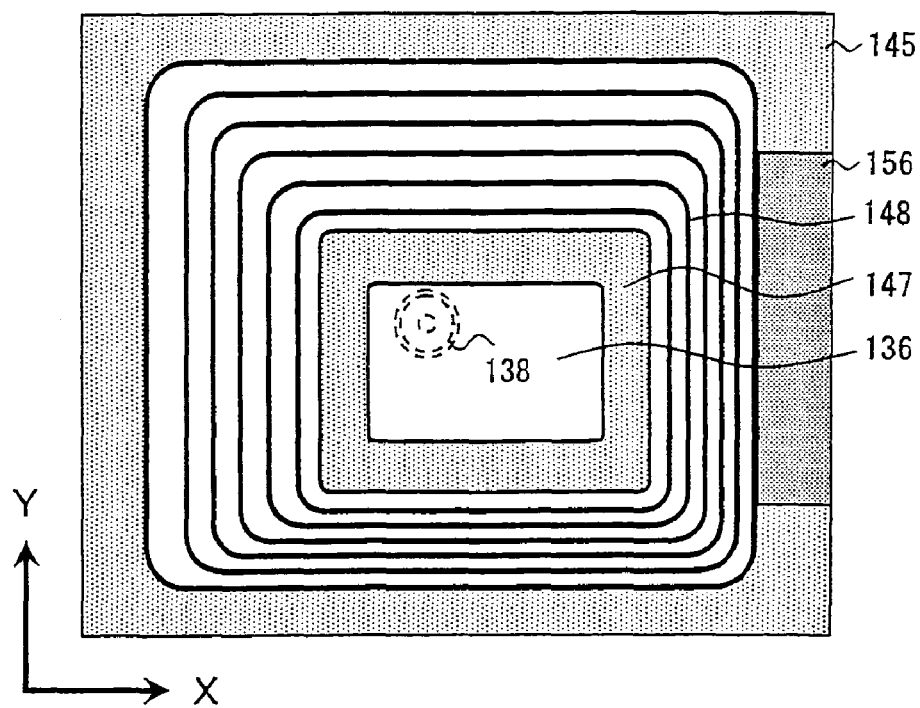

The elastic material 148, as described in FIG. 6 and FIG. 7, is elastic in all circumferential directions in a plane according to the movement of the X stage 146 or the Y stage 147, and therefore robust and soft material such as rubber is required to be used. In addition, material that does not give any effect on cell culture is required and material such as nitrile rubber that has low gas permeation performance is used in an embodiment. Further, the elastic material 148 is made up of such material having low reflection and light-shielding performance, hence the light when observing samples does not cause diffused reflection, neither permeates into the observation chamber 105.

Moreover, the elastic material 148 has to take the "flexure" effectively with expanding and shrinking due to driving stroke of X and Y stages. Therefore, the section shape of the elastic material 148 in the direction of expanding and shrinking is required to have bellows shape. The outer shape of the elastic material 148 in FIG. 7 was a rectangular shape similarly with the shape of the transparent glass stage plate 136. However, the outer shape may be round shape or elliptical shape and so on so that four corners of the elastic material 148 are not burdened when the transparent glass stage plate 136 is moved in X and Y direction.

Figure 8:
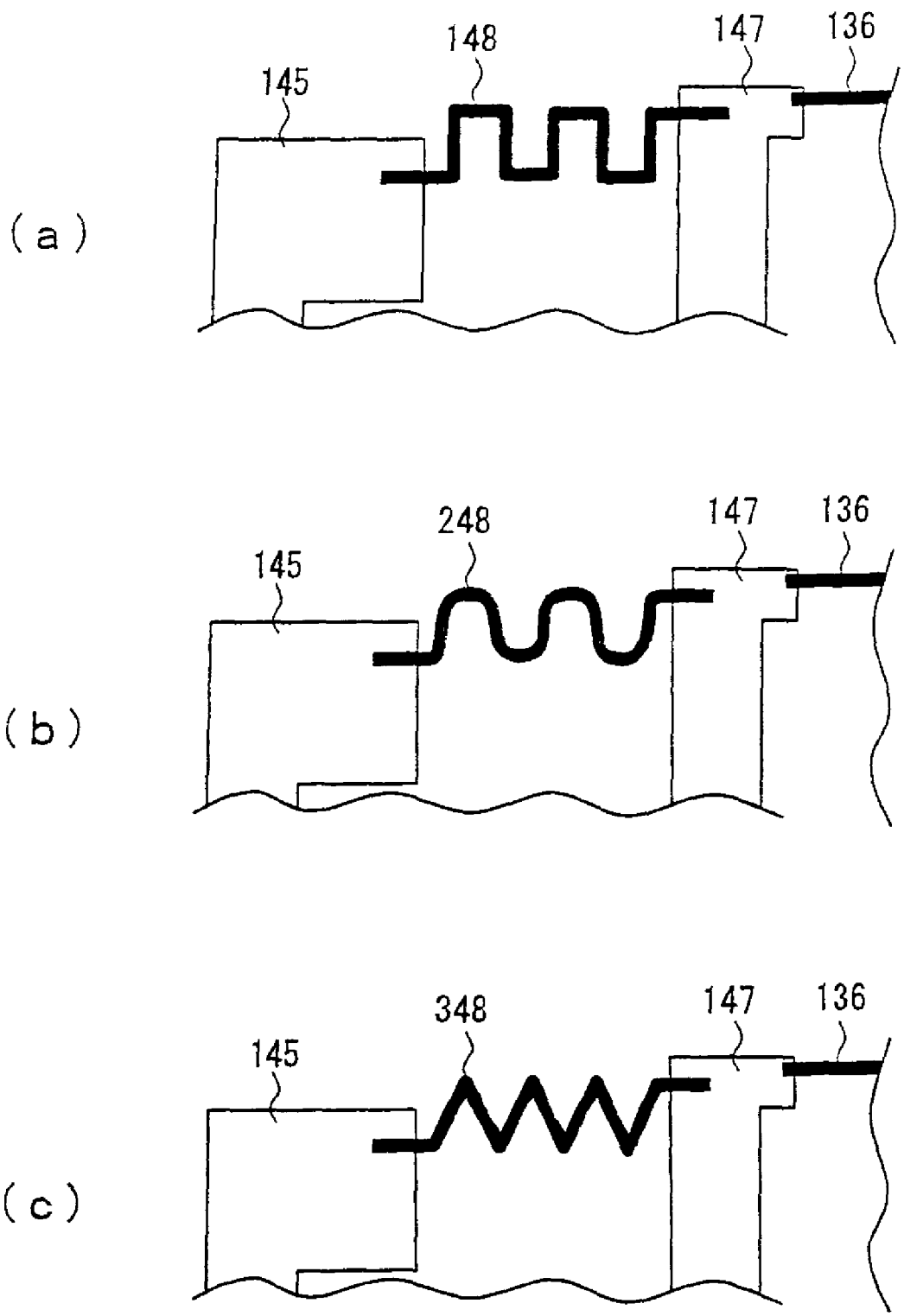
FIGS. 8(a) to 8(c) are cross sections showing a sectional shape of the elastic material.

Next, the bellows shape of the elastic material 148 will be described using FIGS. 8(*a*) to 8(*c*). FIG. 8(*a*) is a diagram showing a situation of a section in the direction of expanding and shrinking the elastic material 148 according to the first embodiment, the section of which is a rectangular shape. In general, a bellows shape used for photograph devices such as camera is triangular shape as the elastic material 348 shown in FIG. 8(*c*), but the stroke when stretched in expanding direction is shorter than that of the rectangular shape and the load required when expanded becomes heavier, resulting in more load in a driving motor. In an embodiment, the rectangular shape shown in FIG. 8(*a*) is employed in order to secure flexure amount when expanded. As shown in the elastic material 248 of FIG. 8(*b*), angled corners of the rectangular may be rounded to be circular arc shape.

As described so far, in the culture observation device 101 according to the present embodiment, driving part such as XY stages for observation is arranged in a side of the observation chamber 105 side separated completely from the culture chamber 102 by a fixed partition including the base plate 106, the stage support stand 145 and the like, and a moving partition (movement stage) including the Y stage 147, and the transparent glass stage plate 136 coupled with the elastic material 148 and the like. Therefore the driving part is not exposed in a high humidity environment of the culture chamber 102. Particularly, as for a stage for observation, stainless steel (martensite) is usually used for the guide rails that perform critical function to obtain stage accuracy. When the XY stages for observation are placed in the culture chamber 102 as in a conventional method, it has been difficult to shut off rust in a high humidity environment of the culture chamber 102. In the present embodiment, however, since the observation chamber 105 is isolated from the culture chamber 102, grease can also be used, which has not been possible to use in the conventional method due to effects on cell culture, and resultantly rust and the like can be prevented.

Moreover, in the present embodiment the fixed partition and the moving partition are coupled with each other via the elastic material 148, however, instead of the elastic material 148, the fixed partition and the moving partition may be arranged so that one of them is put on top of another and a part of the both partition slides on each other, and injection of shielding liquid such as oil and the like in the sliding part enables to separate the culture chamber and the observation chamber.

In addition, motors of the XY stages do not require any countermeasure against the high humidity, and dust generated by sliding of mechanical parts can be shut off. Further, since the section shape of the elastic material 148 in the direction of expanding and shrinking is arranged to be a rectangular shape, the part to be driven in the XY stages is easy to expand as well as causing less load on motors. Particularly it is not necessary to move the heavy microscope as a whole as in a conventional method, thus enabling downsizing and cost-reduction.

Furthermore, the moving partition and the transparent glass stage plate 136 are integrated, therefore working distance of the objective lens 138 of the microscope can be shortened, and accordingly a bright view of observation with high NA can be obtained.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A culture observation equipment comprising:
    a culture chamber;
    an observation chamber having an optical system of observation to observe samples cultured in said culture chamber;
    a movement stage provided at a boundary which separates said culture chamber and said observation chamber, functioning as a wall to maintain an environment of both of said chambers, bearing said samples, and moving said samples on a light axis of observation of said optical system of observation;
    a stage support stand supporting said movement stage; and
    a connecting material being placed between said movement stage and said stage support stand, wherein
    said connecting material expands and shrinks freely between said movement stage and said stage support stand according to a movement of said movement stage.

2. The culture observation equipment according to claim 1, wherein said connecting material is made up of an elastic material having elasticity.

3. The culture observation equipment according to claim 1, wherein said connecting material includes a plate material which supports said movement stage and shielding liquid which lies between said movement stage and said plate material.

4. The culture observation equipment according to claim 2, wherein said connecting material is made up of the elastic material having elasticity, and
    said elastic material is arranged to include rubber provided with flexure being elastic in all circumferential directions.

5. The culture observation equipment according to claim 4, wherein said connecting material is made up of the elastic material having elasticity,
    a section of said elastic material in a direction of expanding and shrinking is formed to have a rectangular shape.

6. The culture observation equipment according to claim 1, further comprising: driving units to drive said movement stage in horizontal direction so as to move a target point of observation of said sample; and optical driving units to drive said optical system of observation in vertical direction so as to focus on said sample.

7. The culture observation equipment according to claim 6, wherein said driving units of said movement stage is disposed on a side of said observation chamber.

8. The culture observation equipment according to claim 1, wherein said movement stage is made up of transparent material and a fixed partition around said movement stage is made up of light shielding material.

9. The culture observation equipment according to claim 1, wherein said connecting material is made up of low reflection and light shielding material.

* * * * *